(12) United States Patent
Kang et al.

(10) Patent No.: US 7,807,461 B2
(45) Date of Patent: Oct. 5, 2010

(54) MULTIPOTENT STEM CELLS DERIVED FROM HUMAN ADIPOSE TISSUE AND CELLULAR THERAPEUTIC AGENTS COMPRISING THE SAME

(75) Inventors: Kyung Sun Kang, Seoul (KR); Jeong Chan Ra, Gyeonggi-do (KR); Jung Ran Park, Seoul (KR)

(73) Assignee: RNL Bio Co., Ltd, Seoul (KR)

( * ) Notice: Subject to any disclaimer, the term of this patent is extended or adjusted under 35 U.S.C. 154(b) by 187 days.

(21) Appl. No.: 11/313,083

(22) Filed: Dec. 20, 2005

(65) Prior Publication Data

US 2007/0110729 A1     May 17, 2007

(30) Foreign Application Priority Data

Nov. 16, 2005  (KR) ............... 10-2005-0109502

(51) Int. Cl.
   C12N 5/071    (2010.01)
   C12N 5/00     (2006.01)
   C12N 5/02     (2006.01)
   A01N 1/00     (2006.01)
   A01N 1/02     (2006.01)

(52) U.S. Cl. .............. 435/366; 435/383; 435/384; 435/1.1

(58) Field of Classification Search ......... 435/366, 435/383, 384, 1.1
   See application file for complete search history.

(56) References Cited

U.S. PATENT DOCUMENTS 6,777,231 B1     8/2004  Katz et al.
2005/0260748 A1*  11/2005 Chang et al. ............. 435/366

FOREIGN PATENT DOCUMENTS

WO     2005085422 A1    9/2005

OTHER PUBLICATIONS

Khan et al., Clin. Exp. Metastasis, 22: 663-673, 2005.*
CD73, CD90, CD29, CD44 and CD105 accessed online at http://www.pathologyoutlines.com/cdmarkers.html on May 5, 2008.*
Hochedlinger et al. Cell, 121: 465-477, May 6, 2005.*
Awad, Hani A., et al., "Chondrogenic differentiation of adipose-derived adult stem cells in agarose, alginate, and gelatin scaffolds", "Biomaterials", Jul. 2004, pp. 3211-3222, vol. 25, No. 16.
Brzoska, Martin, et al., "Epithelial differentiation of human adipose tissue-derived adult stem cells", "Biochemical and Biophysical Research Communications", Apr. 2005, pp. 142-150, vol. 330, No. 1.
Cao, Ying, et al., "Human adipose tissue-derived stem cells differentiate into endothelial cells in vitro and improve postnatal . . . ", "Biochemical and Biophysical Research Communications", Jul. 2005, pp. 370-379, vol. 332, No. 2.
Cousin, Beatrice, et al., "Reconstitution of lethally irradiated mice by cells isolated from adipose tissue", "Biochem. Biophys. Res. Commun.", Feb. 21, 2003, pp. 1016-1022, vol. 301, No. 4.
Fujimura, Juri, et al., "Neural differentiation of adipose-derived stem cells isolated from GFP transgenic mice", "Biochemical and Biophysical Research Communications", Jul. 2005, pp. 116-121, vol. 333, No. 1.
Lin, Tsai-Ming, et al., "Accelerated growth and prolonged lifespan of adipose tissue-derived human mesenchymal stem cells in a medium using . . . ", "Stem Cells and Development", Feb. 2005, pp. 92-102, vol. 14, No. 1.
Arai, F. et al. , "Mesenchymal Stem Cells in Perichondrium Express Activated Leukocyte Cell Adhesion Molecule and Participate in Bone . . . ", "J. Exp. Med.", Jun. 17, 2002, pp. 1549-1563, vol. 195, No. 12, Publisher: The Rockefeller University Press.
Bosch, P. et al. , "Isolation, Characterization, Gene Modification, and Nuclear Reprogramming of Porcine Mesenchymal Stem Cells", "Biology of Reproduction", 2006, pp. 46-57, vol. 74.

(Continued)

*Primary Examiner*—Thaian N Ton
(74) *Attorney, Agent, or Firm*—Kelly K. Reynolds; Steven J. Hultquist; Intellectual Property Technology Law

(57) ABSTRACT

This invention relates to human adipose tissue-derived multipotent adult stem cells. More particularly, the invention relates to human adipose tissue-derived multipotent stem cells, which can be maintained in an undifferentiated state for a long period of time by forming spheres and have high proliferation rates, as well as methods for isolating and maintaining the adult stem cells, and methods for differentiating the multipotent adult stem cells into nerve cells, fat cells, cartilage cells, osteogenic cells and insulin-releasing pancreatic beta-cells. Also, the invention relates to cellular therapeutic agents for treating osteoarthritis, osteoporosis and diabetes and for forming breast tissue, which contain the differentiated cells or the adult stem cells. Although the multipotent stem cells are adult stem cells, they have the ability to differentiate into osteogenic cells, nerve cells, astrocytes, fat cells, chrondrogenic cells or insulin-releasing pancreatic beta-cells, and so are effective in treating osteoporosis, osteoarthritis, nerve disease, diabetes, etc. Also, the stem cells form spheres in a serum-free medium containing CORM-2, and thus can be maintained in an undifferentiated state for a long period of time. Also, the stem cells have very high proliferation rates. Accordingly, the stem cells are useful as cellular therapeutic agents.

4 Claims, 7 Drawing Sheets

OTHER PUBLICATIONS

Fickert, S. et al., "Identification of subpopulations with characteristics of mesenchymal progenitor cells from human osteoarthritic . . .", "Arthritis Research & Therapy", Jul. 19, 2004, pp. R422-R432, vol. 6, No. 5.

Fukuchi, Y. et al., "Human Placenta-Derived Cells Have Mesenchymal Stem/Progenitor Cell Potential", "Stem Cells", 2004, pp. 649-658, vol. 22.

Jones, E. et al., "Isolation and Characterization of Bone Marrow Multipotential Mesenchymal Progenitor Cells", Dec. 2002, pp. 3349-3360, vol. 46, No. 12.

BD Biosciences Division, "BD FACSCalibur Flow Cytometer; The Automated, Multicolor Flow Cytometry System Product Brochure", "BD Bisciences FACS Calibur Product Manual", 2002, pp. 1-11.

Sotiropoulou, P. et al., "Characterization of the Optimal Culture Conditions for Clinical Scale Production of Human Mesenchymal Stem Cells", "Stem Cells", 2006, pp. 462-471, vol. 24.

Zhang, Yi et al., "Comparison of mesenchymal stem cells from human placenta and bone marrow", "Chinese Medical Journal", 2004, pp. 882-887, vol. 117, No. 6.

Gronthos, Stan, et al., Surface protein characterization of human adipose tissue-derived stromal cells, Journal of Cellular Physiology, Aug. 2001, pp. 54-63, vol. 189, No. 1.

Jiang, Yueha, et al., Pluripotency of mesenchymal stem cells derived from adult marrow, Nature, Jul. 2002, pp. 41-49, vol. 418.

Jiang, Yueha, et al., Multipotent progenitor cells can be isolated from postnatal murine bone marrow, mscle, and brain, Experimental Hematology, Aug. 2002, pp. 896-904, vol. 30, No. 8.

Lin, Tsai-Ming, et al., Accelerated growth and prolonged lifespan of adipose tissue-derived human mesenchymal stem cells in a medium using . . . , Stem Cells and Development, Feb. 2005, pp. 92-102, vol. 14, No. 1.

Miranville, A., et al., Improvement of postnatal neovascularization by human adipose tissue-derived stem cells, Circulation, Jul. 2004, pp. 349-355, vol. 110, No. 3.

Ogawa, Rei, et al., Adipogenic differentiation by adipose-derived stem cells harvested from GFP transgenic mice—including relationship . . . , Biochemical and Biophysical Research Communications, Jun. 2004, pp. 511-517, vol. 319, No. 2.

Ogawa, Rei, et al., Osteogenic and chondrogenic differentiation by adipose-derived stem cells harvested from GFP transgenic mice, Biochemical and Biophysical Research Communications, Jan. 2004, pp. 871-877, vol. 313, No. 4.

Rodriguez, Anne-Marie, et al., Adipocyte differentiation of multipotent cells established from human adipose tissue, Biochemical and Biophysical Research Communications, Mar. 2004, pp. 255-263, vol. 315, No. 2.

Safford, Kristine M., et al., Neurogenic differentiation of murine and human adipose-derived stromal cells, Biochemical and Biophysical Research Communications, Jun. 2002, pp. 371-379, vol. 294, No. 2.

Sampaolesi, Maurillo, et al., Cell therapy of alpha-sarcoglycan null dystrophic mice through intra-arterial delivery of mesoangioblasts, Science, Jul. 2003, pp. 487-492, vol. 301, No. 5632.

Seo, Min Jeong, et al., Differentiation of human adipose stromal cells into hepatic lineage in vitro and in vivo, Biochemical and Biophysical Research Communications, Mar. 2005, pp. 258-264, vol. 328, No. 1.

Simmons, D. And Seed, B., Isolation of a cDNA encoding CD33, a differentiation antigen of myeloid progenitor cells, Journal of Immunology, 1988, pp. 2797-2800, vol. 141, No. 8.

Toma, Jean G., et al., Isolation of multipotent adult stem cells from the dermis of mammalian skin, Nature Cell Biology, 2001, pp. 778-784, vol. 3, No. 9.

Verfaille, Catherine M., Adult stem cells: assessing the case for pluripotency, Trends in Cell Biology, Nov. 2002, pp. 502-508, vol. 12, No. 11.

Zuk, Patricia A., et al., Multilineage cells from human adipose tissue: implications for cell-based therapies, Tissue Engineering, Apr. 2001, pp. 211-228, vol. 7, No. 2.

* cited by examiner

Day 1  Day 4

A-1　　　　　　　　　　　　　　A-2

7 days

Day 12

(A) Phase contrast (B) Oil Red O stain (A) Phase contrast (B) Alcian blue stain

C-peptide        Insulin

MULTIPOTENT STEM CELLS DERIVED FROM HUMAN ADIPOSE TISSUE AND CELLULAR THERAPEUTIC AGENTS COMPRISING THE SAME

CROSS-REFERENCE TO RELATED APPLICATION

This application claims the benefit of filling date of Korean Patent Application No. 10-2005-0109502 filed on Nov. 16, 2005, in the Korean Intellectual Property Office, the disclosure of which is incorporated herein in its entirety by reference.

TECHNICAL FIELD

The present invention relates to multipotent adult stem cells derived from human adipose tissue, and more particularly, to human breast adipose tissue-derived multipotent adult stem cells, which can be maintained in a non-differentiated state for a long period of time by forming spheres and have high proliferation rates. Also, the present invention relates to a method for isolating and maintaining the adult stem cells, a method for differentiating the adult stem cells into nerve cells, fat cells, cartilage cells, osteogenic cells and insulin-releasing pancreatic beta-cells, a cellular therapeutic agent for treating osteoarthritis, osteoporosis and diabetes, and a cellular therapeutic agent for forming breast tissue.

BACKGROUND ART $21^{st}$ biotechnology presents the possibility of new solutions to the food, environment and health problems, with the ultimate object of promoting human prosperity. In recent years, the technology of using stem cells has been considered as a new way to treat incurable diseases. Formerly, organ transplantation, gene therapy, etc., were presented for the treatment of incurable human diseases, but their efficient use has not been made due to immune rejection, a short supply of organs, an insufficient development of vectors, and an insufficient knowledge of disease genes.

For this reason, with increasing interests in stem cell studies, it has been recognized that totipotent stem cells having the ability to form all the organs by proliferation and differentiation can not only treat most of diseases but also fundamentally heal organ injuries. Also, many scientists have suggested the applicability of stem cells for the regeneration of all the organs and the treatment of incurable diseases, including Parkinson's disease, various cancers, diabetes and spinal damages.

Stem cells refers to cells having not only self-replication ability but also the ability to differentiate into at least two cells, and can be divided into totipotent stem cells, pluripotent stem cells, and multipotent stem cells.

Totipotent stem cells are cells having totipotent properties capable of developing into one perfect individual, and these properties are possessed by cells up to the 8-cell stage after the fertilization of an oocyte and a sperm. When these cells are isolated and transplanted into the uterus, they can develop into one perfect individual.

Pluripotent stem cells, which are cells capable of developing into various cells and tissues derived from the ectodermal, mesodermal and endodermal layers, are derived from an inner cell mass located inside of blastocysts generated 4-5 days after fertilization. These cells are called "embryonic stem cells" and can differentiate into various other tissue cells but not form new living organisms.

Multipotent stem cells, which are stem cells capable of differentiating into only cells specific to tissues and organs containing these cells, are involved not only in the growth and development of various tissues and organs in the fetal, neonatal and adult periods but also in the maintenance of homeostasis of adult tissue and the function of inducing regeneration upon tissue damage. Tissue-specific multipotent cells are collectively called "adult stem cells".

Adult stem cells are obtained by taking cells from various human organs and developing the cells into stem cells and are characterized in that they differentiate into only specific tissues. However, recently, experiments for differentiating adult stem cells into various tissues, including liver cells, were dramatically successful.

The multipotent stem cells were first isolated from adult marrow (Jiang et al., *Nature*, 418:41, 2002), and then also found in other various adult tissues (Verfaillie, *Trends Cell Biol.*, 12:502, 2002). In other words, although the marrow is the most widely known source of stem cells, the multipotent stem cells were also found in the skin, blood vessels, muscles and brains (Tomas et al., *Nat. Cell Biol.*, 3:778, 2001; Sampaolesi et al., *Science*, 301:487, 2003; Jiang et al., *Exp. Hematol.*, 30:896, 2002). However, stem cells in adult tissues, such as the marrow, are very rarely present, and such cells are difficult to culture without inducing differentiation, and so difficult to culture in the absence of specifically screened media. Namely, it is very difficult to maintain the isolated stem cells in vitro.

Recently, adipose tissue was found to be a new source of multipotent stem cells (Cousin et al., *BBRC.*, 301:1016, 2003; Miranville et al., *Circulation*, 110:349, 2004; Gronthos et al., *J. Cell Physiol.*, 189:54, 2001; Seo et al., *BBRC.*, 328:258, 2005). Namely, it was reported that a group of undifferentiated cells is included in human adipose tissue obtained by liposuction and has the ability to differentiate into fat cells, osteogenic cells, myoblasts and chondroblasts (Zuk et al., *Tissue Eng.*, 7:211, 2001; Rodriguez et al., *BBRC.*, 315:255, 2004). This adipose tissue has an advantage in that it can be extracted in large amounts, and thus, it receives attention as a new source of stem cells, which overcomes the existing shortcomings.

Also, recent studies using animal model experiments indicate that adipose tissue-derived cells have the abilities to regenerate muscles and to stimulate the differentiation of nerve blood vessels. Thus, these adipose tissue-derived cells have attention as a new source of stem cells.

Adipose tissue-derived stem cells known till now include human adipose-derived adult stem cells that can differentiate into epithelial cells (Brzoska et al., *BBRC*, 330:142, 2005), human adipose-derived adult stem cells that can differentiate into osteogenic and fat cells (Cao et al., *BBRC*, 332:370, 2005), human adipose-derived adult stem cells that can differentiate into nerve cells (Safford et al., *BBRC*, 294:371, 2002), rat adipose-derived stem cells that can differentiate into fat cells (Ogawa et al., *BBRC*, 319:511, 2004), rat adipose-derived stem cells that can differentiate into osteogenic and chondrogenic cells (Ogawa et al., *BBRC*, 313:871, 2004), human adipose-derived stem cells that can differentiate into cartilage cells (*Biomaterials*, 25:3211, 2004), rat adipose-derived stem cells that can differentiate into nerve cells (Fujimura et al., *BBRC*, 333:116, 2005), and adipose-derived stem cells that can differentiate into bone cells, cartilage cells, nerve cells or muscle cells (U.S. Pat. No. 6,777,231).

However, most of adipose-derived stem cells known till now are stem cells derived from the adipose tissue of animals other than human beings. Even if they are stem cells derived from human adipose tissue, they have been limited to those derived from tissues obtained by the liposuction of abdominal fat, and the kind of cells differentiated from the stem cells has also been limited. Particularly, isolated stem cells have low proliferation rates and are difficult to maintain in an undifferentiated state for a long period of time, and thus, have been limited in application.

Accordingly, the present inventors have made extensive efforts to develop multipotent adult stem cells, which have high proliferation rates, can be maintained in a undifferentiated state for a long period of time by forming spheres and can differentiate into more various cells, as a result, found that multipotent stem cells isolated from human adipose tissue can differentiate into various cells, including osteogenic cells, chondrogenic cells, nerve cells, astrocytes, fat cells, and insulin-releasing pancreatic beta-cells, have a very high proliferation rate and can be maintained in an undifferentiated state for a long period of time by forming spheres, thereby completing the present invention.

SUMMARY OF THE INVENTION

Therefore, it is an object of the present invention to provide human adipose tissue-derived multipotent adult stem cells, which have high proliferation rates and can be maintained in an undifferentiated state for a long period of time by forming spheres, as well as a production method thereof.

Another object of the present invention is to provide a method for differentiating said multipotent stem cells into nerve cells, astrocytes, cartilage cells, osteogenic cells, fat cells and insulin-releasing pancreatic beta-cells, as well as cellular therapeutic agents containing said differentiated cells or adult stem cells.

To achieve the above objects, in one aspect, the present invention provides a method for producing adult stem cells, comprising culturing human adipose tissue-derived pellets in a medium containing N-acetyl-L-cysteine (NAC) and then collecting the cultured cells, the adult stem cells being characterized by: (a) showing positive immunological responses to all of CD73, CD90, CD29, CD44 and CD105, and negative immunological responses to all of CD33, CD34, CD45, CD4, CD31, CD62p, CD14 and HLA-DR; (b) growing attached to a plastic material, showing spindle-shaped morphological features, and forming spheres in a medium containing CORM-2 so as to be able to be maintained in an undifferentiated state for a long period of time; and (c) having the ability to differentiate into mesoderm-derived cells.

In the present invention, the NAC-containing medium additionally contains ascorbic acid, calcium, rEGF, BPE, insulin and hydrocortisone.

In another aspect, the present invention provides a method for maintaining adult stem cells in an undifferentiated state, the method comprising culturing adult stem cells prepared by said method in a medium containing CORM-2 so as to form spheres.

In the present invention, the CORM-2-containing medium is preferably a serum-free medium, which additionally contains antibiotic antimycotic solution, hydrocortisone, insulin, rEGF, FGF, B27 and β-mercaptoethanol.

In still another aspect, the present invention provides adult stem cells produced by said method and characterized by: (a) showing positive immunological responses to all of CD73, CD90, CD29, CD44 and CD105, and negative immunological responses to all of CD33, CD34, CD45, CD4, CD31, CD62p, CD14 and HLA-DR; (b) growing attached to a plastic material, showing spindle-shaped morphological features, and forming spheres in a medium containing CORM-2 so as to be able to be maintained in an undifferentiated state for a long period of time; and (c) having the ability to differentiate into mesoderm-derived cells.

In the present invention, the adult stem cells are preferably cultured in an undifferentiated state for at least 16 passages, and the mesoderm-derived cells are preferably cartilage cells, osteogenic cells, nerve cells, astrocytes, fat cells and insulin-releasing pancreatic beta-cells.

In still another aspect, the present invention provides a method for differentiating adult stem cells into nerve cells, the method comprising the steps of: (a) preincubating the adult stem cells in a DMEM medium containing BME and FBS; and (b) treating the preincubated broth with DMSO and BHA so as to induce differentiation into nerve cells. Also, the present invention provides a cellular therapeutic agent for treating nerve disease, which contains said differentiated nerve cells as active ingredients.

In still another aspect, the present invention provides a method for differentiating adult stem cells into cartilage cells, the method comprising culturing the adult stem cells in an α-MEM medium containing TFG-β1, L-ascorbate-2-phosphate and insulin. Also, the present invention provides a cellular therapeutic agent for treating osteoarthritis, which contains said differentiated cartilage cells as active ingredients.

In still another aspect, the present invention provides a method for differentiating adult stem cells into osteogenic cells, the method comprising mixing the adult stem cells with tricalcium phosphate (TCP) and isotransplanting the mixture. Also, the present invention provides a cellular therapeutic agent for treating bone deficiency, which contains said differentiated osteogenic cells as active ingredients.

In still another aspect, the present invention provides a method for differentiating adult stem cells into fat cells, the method comprising culturing the adult stem cells in an α-MEM medium containing dexamethasone, indomethacin, insulin and IBMX. Also, the present invention provides a cellular therapeutic agent for forming breast tissue, which contains said differentiated fat cells as active ingredients.

In still another aspect, the present invention provides a method for differentiating adult stem cells into insulin-releasing pancreatic beta-cells, the method comprising the steps of: (a) culturing the adult stem cells in low-glucose DMEM medium containing nicotinamide, β-mercaptoethanol and FBS for 12-72 hours; and (b) culturing the cultured cells in high-glucose DMEM medium containing nicotinamide, β-mercaptoethanol and FBS for 4-7 days. Also, the present invention provides a cellular therapeutic agent for treating diabetes, which contains said differentiated insulin-releasing pancreatic beta-cells as active ingredients.

In still another aspect, the present invention provides a cellular therapeutic agent for treating nerve disease containing the adult stem cells having the ability of differentiation into nerve cells, as active ingredients.

In still another aspect, the present invention provides a cellular therapeutic agent for treating diabetes containing the adult stem cells having the ability of differentiation into insulin-releasing pancreatic beta-cells, as active ingredients.

In still another aspect, the present invention provides a cellular therapeutic agent for treating osteoarthritis containing the adult stem cells having the ability of differentiation into cartilage cells, as active ingredients.

In still another aspect, the present invention provides a cellular therapeutic agent for treating bone deficiency containing the adult stem cells having the ability of differentiation into osteogenic cells, as active ingredients.

In still another aspect, the present invention provides a cellular therapeutic agent for forming breast tissue containing the adult stem cells having the ability of differentiation into fat cells, as active ingredients.

The above and other objects, features and embodiments of the present invention will be more clearly understood from the following detailed description and the accompanying claims.

DETAILED DESCRIPTION OF THE INVENTION, AND PREFERRED EMBODIMENTS

Figure 1:
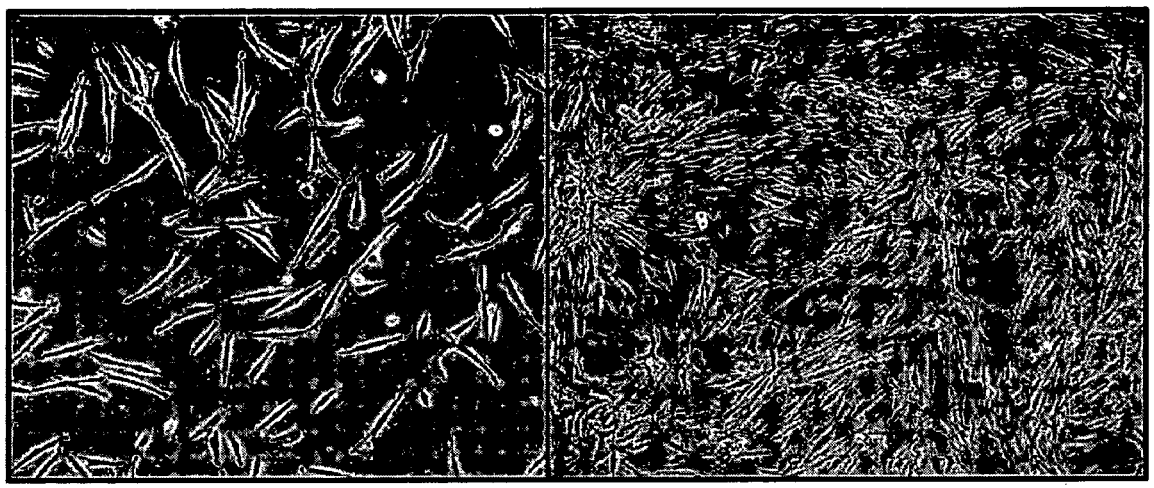
FIG. 1 shows photographs taken at 100× magnification for human adipose tissue-derived multipotent stem cells according to the present invention.

The present invention relates to multipotent stem cells isolated from human breast adipose tissue.

In the present invention, multipotent stem cells were first isolated and purified from human breast adipose tissue in the following manner. The isolated human adipose tissue was washed with PBS, and finely cut and then digested in a DMEM medium supplemented with collagenase type 1 (1 mg/ml), at 37° for 2 hours. After washing with PBS, the tissue was centrifuged at 1000 rpm for 5 minutes. The supernatant was suctioned off, and the pellets remaining on the bottom were washed with PBS and then centrifuged at 1000 rpm for 5 minutes. The resulting pellets were filtered through a 100-μm mesh to remove debris, followed by washing with PBS. Then, the pellets were incubated in a DMEM medium (10% FBS, 2 mM NAC, 0.2 mM ascorbic acid). After one overnight period, unattached cells were washed off with PBS, and the remaining cells were cultured in a K-NAC media (Keratinocyte-SFM media+2 mM NAC+0.2 mM ascorbic acid+0.09 mM calcium+5 ng/ml rEGF+50 μg/ml BPE+5 g/ml insulin+74 ng/ml hydrocortisone) while the media were replaced at two-day intervals, thereby obtaining human breast adipose tissue-derived multipotent stem cell solution.

The proliferation rate of the isolated human breast adipose tissue-derived multipotent stem cells was examined, as a result, it was found that CPDL was gradually increased up to a passage number of 16, indicating that the stem cells have high proliferation rates.

Meanwhile, for the sphere culture of stem cells, $5 \times 10^4$-$1 \times 10^5$ cells/ml of the isolated adipose tissue-derived multipotent stem cells were seeded into each well of a 6-well plate, which contains MEBM medium (10 μM CORM-2 (tricarbonyldichlororuthenium(II) dimer), B27, 5 ml antibiotic antimycotic solution (100×), 1 μg/ml hydrocortisone, 5 μg/ml insulin, 20 ng/ml EGF, 40 ng/ml FGF and β-mercaptoethanol), as a result, they started to form spheres from 3 days after the seeding. This suggests that the stem cells have high proliferation rates while being maintained in an undifferentiated state.

Methods of obtaining multipotent stem cells expressing the desired surface antigens from the human adipose tissue-derived stem cell broth obtained above include a FACS method using a flow cytometer with sorting function (*Int. Immunol.*, 10(3):275, 1998), a method using magnetic beads, and a panning method using an antibody specifically recognizing multipotent stem cells (*J. Immunol.*, 141(8):2797, 1998). Also, methods for obtaining multipotent stem cells from a large amount of culture broth include a method where antibodies specifically recognizing molecules expressed on the surface of cells (hereinafter, referred to as "surface antigens") are used alone or in combination as columns.

Flow cytometry sorting methods may include a water drop charge method and a cell capture method. In any of these methods, an antibody specifically recognizing an antigen on the cell surface is fluorescently labeled, the intensity of fluorescence emitted from an antibody bonded with the molecule expressed on the surface of the cell is converted to an electric signal whereby the expressed amount of the antigen can be quantified. It is also possible to separate cells expressing a plurality of surface antigens by combination of fluorescence types used therefor. Examples of fluorescences which can be used in this case include FITC (fluorescein isothiocyanate), PE (phycoerythrin), APC (allo-phycocyanin), TR (Texas Red), Cy 3, CyChrome, Red 613, Red 670, TRI-Color, Quantum Red, etc.

FACS methods using a flow cytometer include: a method where the above stem cell broth is collected, from which cells are isolated by, for example, centrifugation, and stained directly with antibodies; and a method where the cells are cultured and grown in a suitable medium and then stained with antibodies. The staining of cells is performed by mixing a primary antibody recognizing a surface antigen with a target cell sample and incubating the mixture on ice for 30 minutes to 1 hour. When the primary antibody is fluorescently labeled, the cells are isolated with a flow cytometer after washing. When the primary antibody is not fluorescently labeled, cells reacted with the primary antibody and a fluorescent labeled secondary antibody having binding activity to the primary antibody are mixed after washing, and incubated on ice water for 30 minutes to 1 hour. After washing, the cells stained with the primary and secondary antibodies are isolated with a flow cytometer.

Various surface antigens may include hematopoietic-associated antigens, the surface antigens of mesenchymal cells, and antigens specific to nervous system neurons. The hematopoietic-associated antigens include CD34, CD45, etc., the surface antigens of mesenchymal cells include SH-2, SH-3, etc., and the antigens specific to nervous system neurons include NSE, GFAP, etc. The single or combined use of antibodies recognizing the above-described surface antigens allows the desired cells to be obtained.

The isolated multipotent adult stem cells according to the present invention were analyzed using a flow cytometer, as a result, showed positive responses to CD73, CD90, CD29, CD44, and CD105. Also, the multipotent stem cells showed negative immunological responses to all of CD33, CD34, CD45, CD4, CD31, CD62p, CD14 and HLA-DR.

In addition, it was found that the isolated multipotent adult stem cells according to the present invention are multipotent stem cells, which can differentiate into nerve cells, astrocytes, osteogenic cells, cartilage cells, fat cells and insulin-releasing pancreatic beta-cells.

EXAMPLES

Hereinafter, the present invention will be described in more detail by examples. It is to be understood, however, that these examples are for illustrative purpose only and are not construed to limit the scope of the present invention.

Example 1

Isolation of Multipotent Stem Cells from Adipose Tissue

Adipose tissue was isolated from women's breast tissue distributed by Breast Cancer Center, Seoul National University, and washed with PBS and then finely cut. The cut tissue was digested in DMEM media supplemented with collagenase type 1 (1 mg/ml), at 37° for 2 hours. The digested tissue was washed with PBS and then centrifuged at 1000 rpm for 5 minutes. The supernatant was suctioned off, and the pellets remaining on the bottom were washed with PBS and then centrifuged at 1000 rpm for 5 minutes. The resulting pellets were filtered through a 100 μm mesh to remove debris, followed by washing with PBS. The resulting cells were incubated in a DMEM medium (10% FBS, 2 mM NAC, 0.2 mM ascorbic acid). After one overnight period, unattached cells were washed with PBS, and cultured in Keratinocyte-SFM media (containing 2 mM NAC, 0.2 mM ascorbic acid, 0.09 mM calcium, 5 ng/ml rEGF, 50 μg/ml BPE, 5 μg/ml insulin and 74 ng/ml hydrocortisone) while the media were replaced at two-day intervals, thus isolating multipotent stem cells. FIG. 1 shows photographs taken at 100× magnification for the human adipose tissue-derived multipotent stem cells isolated as described above.

Example 2

Examination of Proliferation Rate of Adipose Tissue-Derived Stem Cells

Adipose tissue was obtained from each of different human breast tissue samples according to the isolation method as described in Example 1. In order to examine the proliferation rate of multipotent stem cells derived from the isolated human breast adipose tissue, $2\times10^5$ of the cells were seeded into a T-75 flask and then measured for CPDL (cumulative population doubling level) and expressed as a function of passage number. CPDL is an index indicative of the proliferation rate of cells and expressed as the following equation.

$$CPDL = \ln(Nf/Ni)/\ln 2, \text{ wherein } Ni: \text{ the initial number of seeded cells; and } Nf: \text{ the final number of cells.}$$

Figure 2:
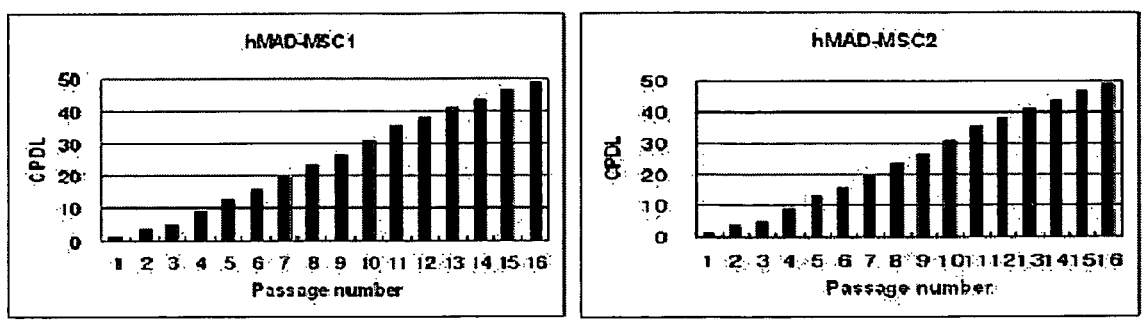
FIG. 2 shows the cumulative population doubling level (CPDL) of human adipose tissue-derived multipotent stem cells according to the present invention. A-1 and A-2: human adipose tissue-derived multipotent stem cells according to the present invention; and B and C: adipose-derived stem cells according to the prior art.
Figure 2:
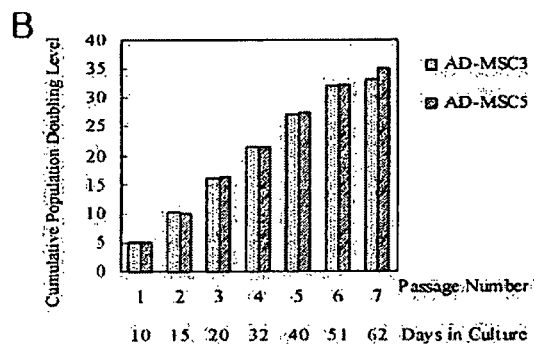
Figure 2:
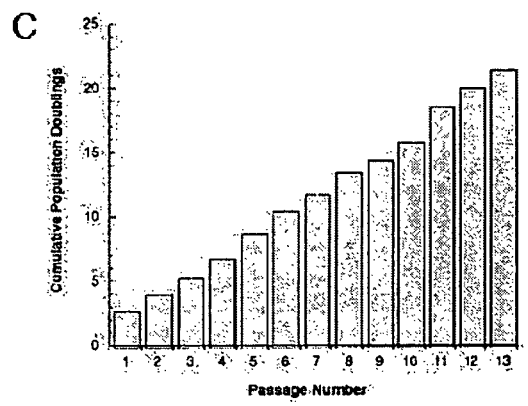

As a result, as shown in "A-1" and "A-2" of FIG. 2, the adult stem cells (hMAD-MCS1 and hMAD-MCS2) according to the present invention showed a CPDL value of about 50 at a passage number of 16.

Meanwhile, "B" and "C" of FIG. 2 show the CPDL values of the prior human adipose tissue-derived stem cells (Lin et al., *Stem Cells and Development*, 14:92, 2005; Zuk et al., *Tissue Eng.*, 7:211, 2001) as a function of passage number. As shown in FIG. 2, the CPDL values of the cells were 30-35 and 21 at passage numbers of 7 and 13, respectively.

These results suggest that the adult stem cells according to the present invention have very high proliferation rates.

Example 3

Immunological Characteristics of Adipose-Derived Multipotent Stem Cells

The adipose tissue-derived multipotent stem cells obtained in Example 1 were washed with PBS and treated with trypsin. The treated cells were collected and centrifuged at 1000 rpm for 5 minutes. The supernatant was discarded and then washed with a mixture of 2% FBS and PBS, followed by centrifugation at 1000 rpm for 5 minutes. The supernatant was discarded, and the cells were suspended in PBS, and $1\times10^5$ cells for each sample were dispensed into a well plate. An antibody (R-phycoerythrin-conjugated mouse anti-human monoclonal antibody) was placed into each well and incubated on ice for 40 minutes. After the incubation, the medium was centrifuged at 1000 rpm for 5 minutes. The supernatant was removed and the cells were washed with PBS and centrifuged at 1000 rpm for 5 minutes. Once again, the supernatant was removed, and the cells were washed with PBS and centrifuged at 1000 rpm for 5 minutes. After removing the supernatant, the cells were fixed with 1% paraformaldehyde and analyzed using a flow cytometer.

TABLE 1

FACS analysis of surface antigens of adipose-derived stem cells

| Antigen | AD-MSCs |
|---------|---------|
| CD73    | +       |
| CD90    | +       |
| CD29    | +       |
| CD44    | +       |
| CD105   | +       |
| CD33    | −       |
| CD34    | −       |
| CD45    | −       |
| CD4     | −       |
| CD31    | −       |
| CD62p   | −       |
| CD14    | −       |
| HLA-DR  | −       |

As a result, as shown in Table 1, the adipose tissue-derived adult stem cells according to the present invention showed positive responses of 91% to CD73, 97% to CD90, 96% to CD29, 83% to CD44, and 80% to CD105. Also, the inventive stem cells showed negative immunological responses to all of CD33, CD34, CD45, CD4, CD31, CD62p, CD14 and HLA-DR.

Example 4

Figure 3:
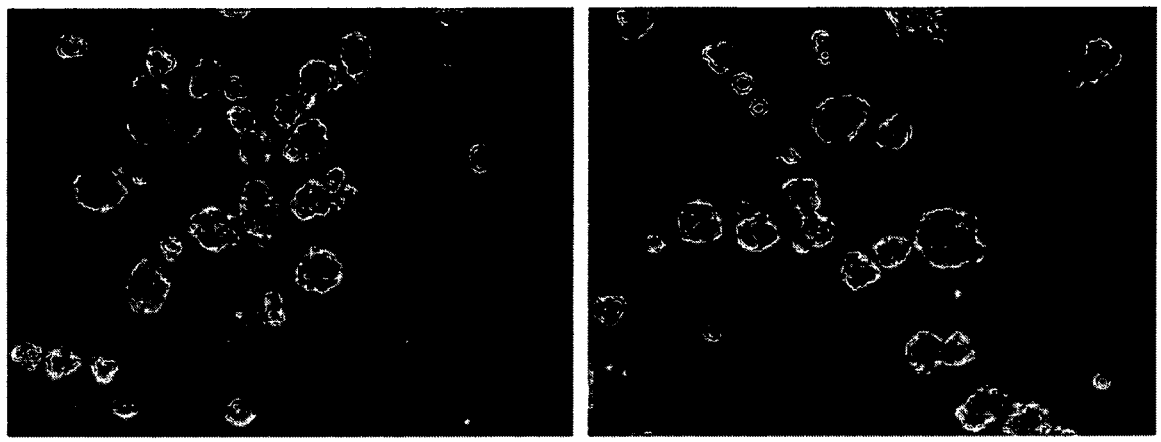
FIG. 3 shows photographs taken at 200× magnification for spheres formed at 7 days after culturing human breast adipose tissue-derived multipotent stem cells according to the present invention.
Figure 4:
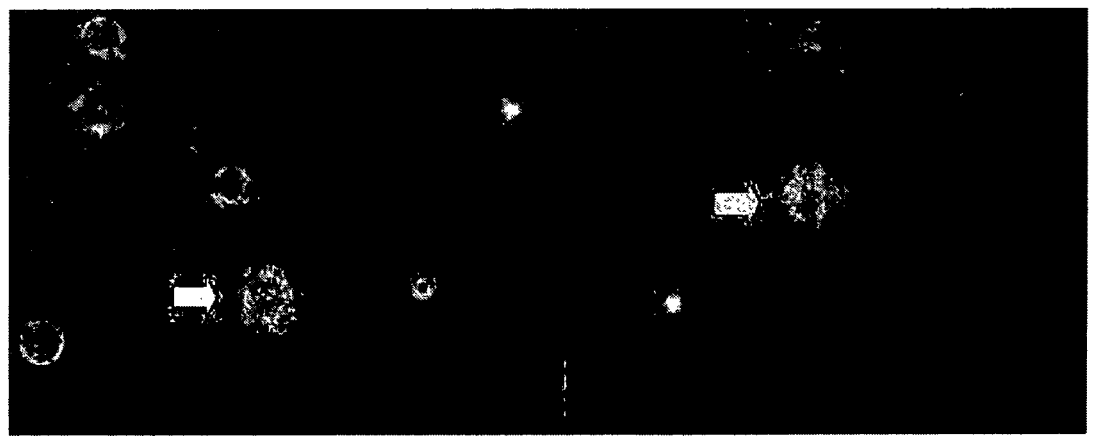
FIG. 4 is a photograph taken at 200× magnification for the shape of a sphere formed by the proliferation of a stem cell in agar.

Sphere Formation of Adipose Tissue-Derived Multipotent Stem Cells $5 \times 10^4$-$1 \times 10^5$/ml of the human breast adipose tissue-derived multipotent stem cells obtained in Example 1 were seeded into each well of a 6-well plate containing a serum-free MEBM medium containing 10 μM CORM-2, 5 ml antibiotic antimycotic solution (100×), 1 μg/ml hydrocortisone, 5 μg/ml insulin, 20 ng/ml EGF, 40 ng/ml FGF, B27 and β-mercaptoethanol. As a result, the cells started to form the shape of spheres from 3-7 days after the seeding, and as shown in FIG. 3 and FIG. 4, the cells proliferated to form spheres even at 7-10 days after the seeding.

Also, the stem cells according to the present invention were cultured in agar. As a result, as shown in FIG. 4, the cells formed spheres.

Figure 5:
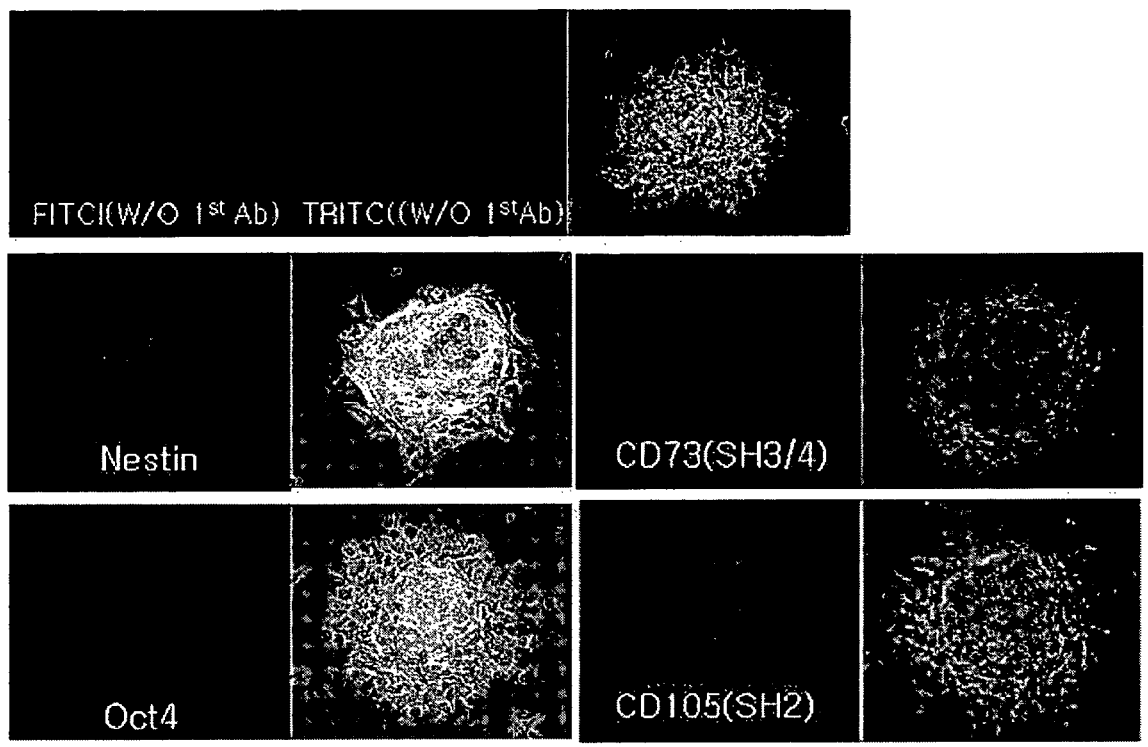
FIG. 5 illustrates photographs taken at 100× magnification, which show the expression of Nestin, Oct4, SH2, SH3/4 in the inventive human adipose tissue-derived multipotent stem cells, which were sphere-cultured in a CORM-2-containing MEBM medium and then immunostained.

Meanwhile, $5 \times 10^4$ stem cells obtained in Example 1 were seeded into each well of a 24-well plate and measured for the number of spheres at each passage number (see Table 2). As a result, as shown in Table 2, the cells maintained spheres, indicating that the cells can be proliferated and maintained for a long period of time. Also, as shown in FIG. 5, Oct4 was positively expressed, indicating that the cells have a high proliferation rate while being maintained in an undifferentiated state.

TABLE 2

| Passage number | Number of spheres |
| --- | --- |
| 1 | 270 |
| 2 | 260 |
| 3 | 271 |

Example 5

Immunostaining Analysis of Adipose Tissue-Derived Stem Cells

The adipose tissue-derived stem cell spheres obtained in Example 4 were washed three times with PBS and fixed with 4% paraformaldehyde-containing PBS for 30 minutes. After washing three times with PBS, the spheres were permeated with PBS containing 0.1% Triton-X100 for 10 minutes. After being washed three times with PBS, the spheres were allowed to react with 10% NGS for 1 hour and then with PBS containing a primary antibody overnight. After washing three times with PBS, the spheres were allowed to react with a secondary antibody in a dark room for 1 hour. After being washed three times with PBS, the spheres were As a result, as shown in FIG. 5, the multipotent stem cell spheres according to the present invention showed positive responses to all of Nestin, which can be regarded as a marker of nerve progenitor cells, Oct4, which can be regarded as a marker of undifferentiated cells, and SH2(CD105) and SH3/4(CD73), which are markers of mesenchymal stem cells.

Example 6

Figure 6:
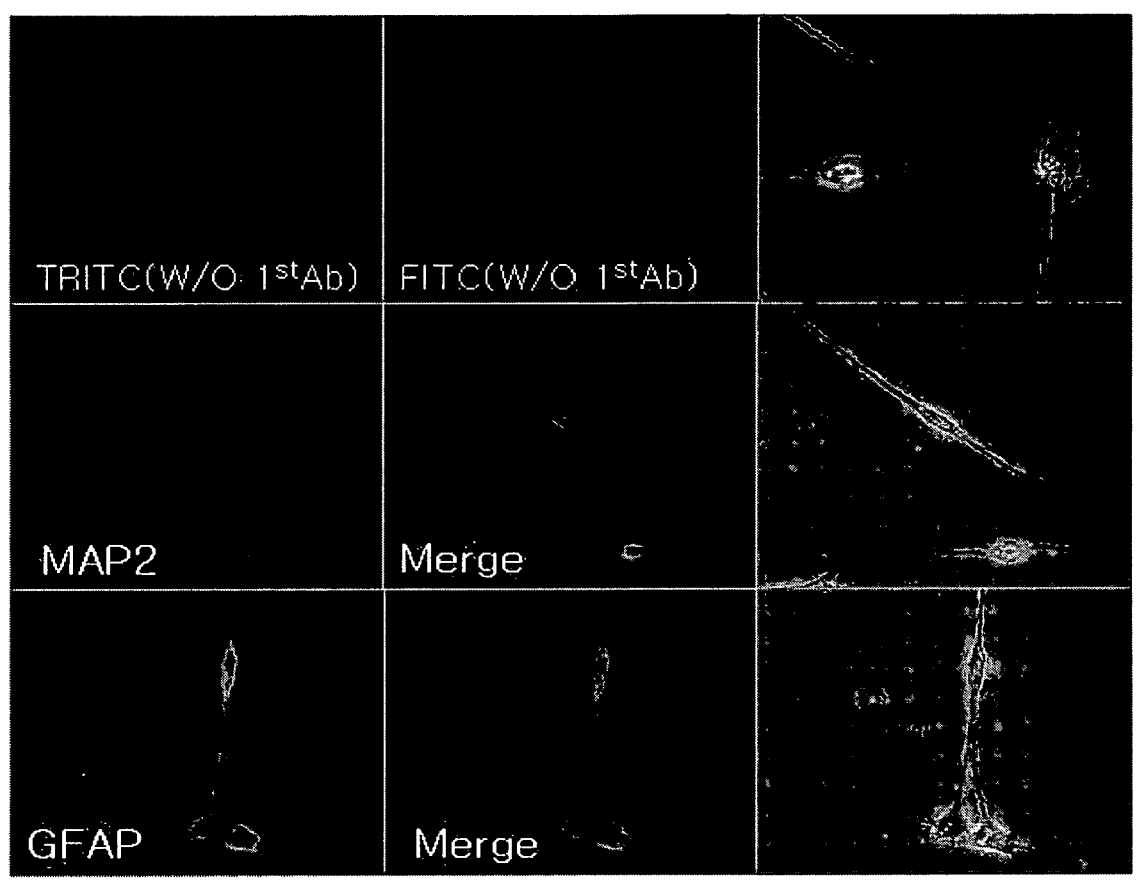
FIG. 6 shows that human adipose tissue-derived multipotent stem cells according to the present invention were differentiated into nerve cells and astrocytes.

Differentiation of Adipose-Derived Multipotent Stem Cells into Nerve Cells and Astrocytes The adipose tissue-derived multipotent stem cells obtained in Example 1 were preincubated in a DMEM medium supplemented with 1 mM BME and 10% FBS, for 24 hours. After the preincubation, the stem cells were incubated in a medium for inducing nerve cell differentiation, containing 1% DMSO and 100 μM BHA (butylated hydroxyanisole), for 90 minutes, so as to induce differentiation into nerve cells, followed by immunostaining (FIG. 6). As a result, as shown in FIG. 6, the human adipose tissue-derived multipotent stem cells according to the present invention showed positive responses to GFAP (glial fibrillary acidic protein), which is an antigen specific to astrocytes in the nervous system, and MAP2 (microtubule-associated protein2), which is a nerve cell-specific substance.

Photographs on the first line in FIG. 6 show results for a negative control group, which indicate that differentiated cells do not show the fluorescence of FITC and TRITC by themselves. The MAP2 photograph at the left side of the second line shows the red fluorescence of TRITC, indicating that MAP2 was expressed. From the phase contrast photograph and the Merge photograph, it was found that the red fluorescence was a fluorescence emitted from cells in which MAP2 was expressed. Also, the GFAP photograph at the left side of the third line showed the green fluorescence of FITC, and from the phase contrast photograph and the Merge photograph, it was seen that the green fluorescence was a fluorescence emitted from cells in which GFAP was expressed. These results suggest that the human adipose-derived multipotent stem cells according to the present invention differentiate into nerve cells and astrocytes.

Example 7

Differentiation of Adipose-Derived Multipotent Stem Cells into Fat Cells

Figure 7:
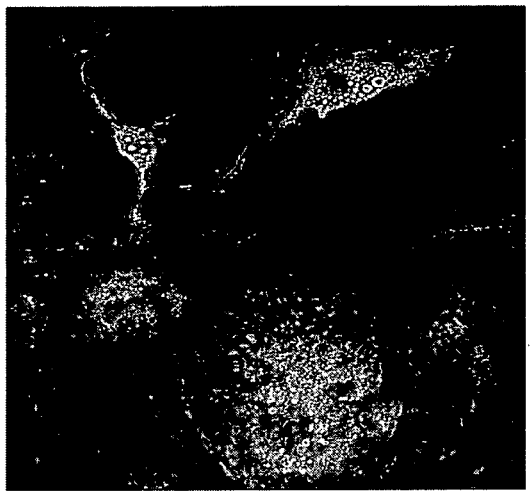
FIG. 7 shows photographs taken at 200× magnification for fat cells differentiated from human adipose tissue-derived multipotent stem cells according to the present invention. A: differentiated phase contrast; and B: stained by oil red O staining.
Figure 7:
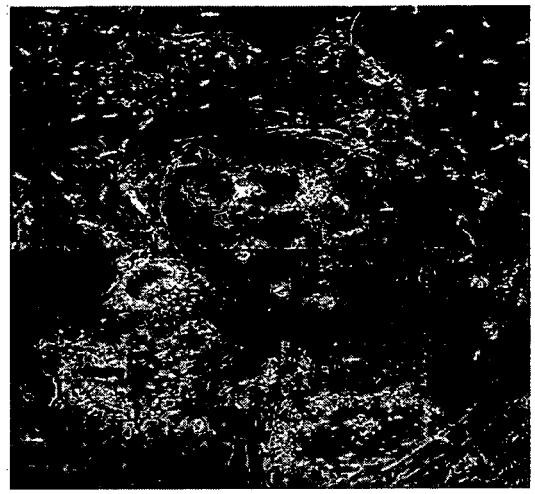

The adipose tissue-derived multipotent stem cells obtained in Example 1 were incubated in an α-MEM medium containing 5% FBS, 1 μM dexamethasone, 200 μM indomethacin, 10 μg/ml insulin and 0.5 mM IBMX (3-isobutyl-1-methylxanthine) for 2 weeks to induce differentiation into fat cells and then analyzed using an oil red O staining method. As a result, as shown in FIG. FIG. 7, it was observed that the human adipose tissue-derived multipotent stem cells were differentiated into fat cells.

Example 8

Figure 8:
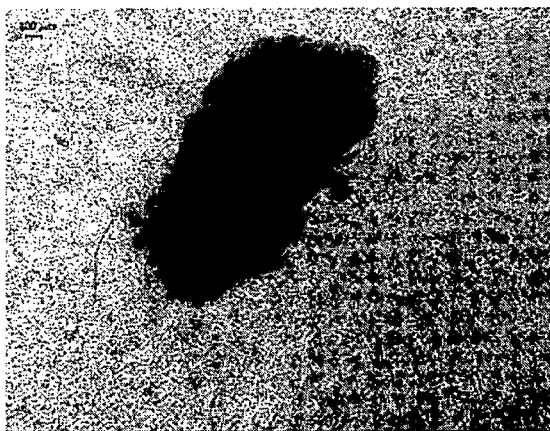
FIG. 8 shows photographs taken at 100× magnification for cartilage cells differentiated from human adipose tissue-derived multipotent stem cells according to the present invention. A: differentiated phase contrast; and B: Alcian blue staining results showing differentiation into cartilage cells.
Figure 8:
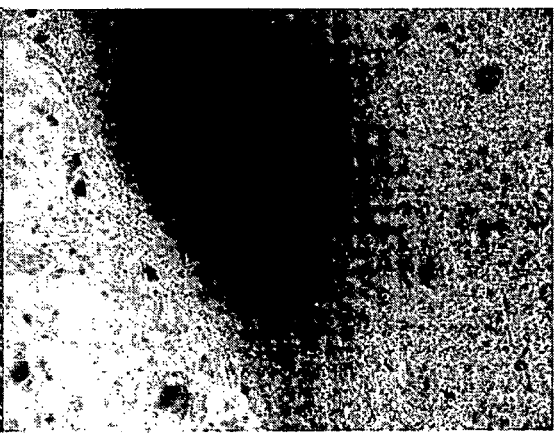

Differentiation of Adipose-Derived Multipotent Stem Cells into Cartilage Cells $10^7$ cells/ml of the adipose tissue-derived multipotent stem cells obtained in Example 1 were dispensed into each center of a 24-well plate in an amount of 10 μl. Then, the cells were incubated in an α-MEM medium containing 5% FBS, 10 ng/ml TFG-β1, 50 μM L-ascorbate-2-phosphate and 6.25 μg/ml insulin for 2 weeks so as to induce differentiation into cartilage cells. Then, whether the multipotent stem cells were differentiated into cartilage cells was analyzed using the Alcian blue staining method. As a result, as shown in FIG. 8, the human adipose tissue-derived multipotent stem cells were differentiated into cartilage cells.

Example 9

Figure 9:
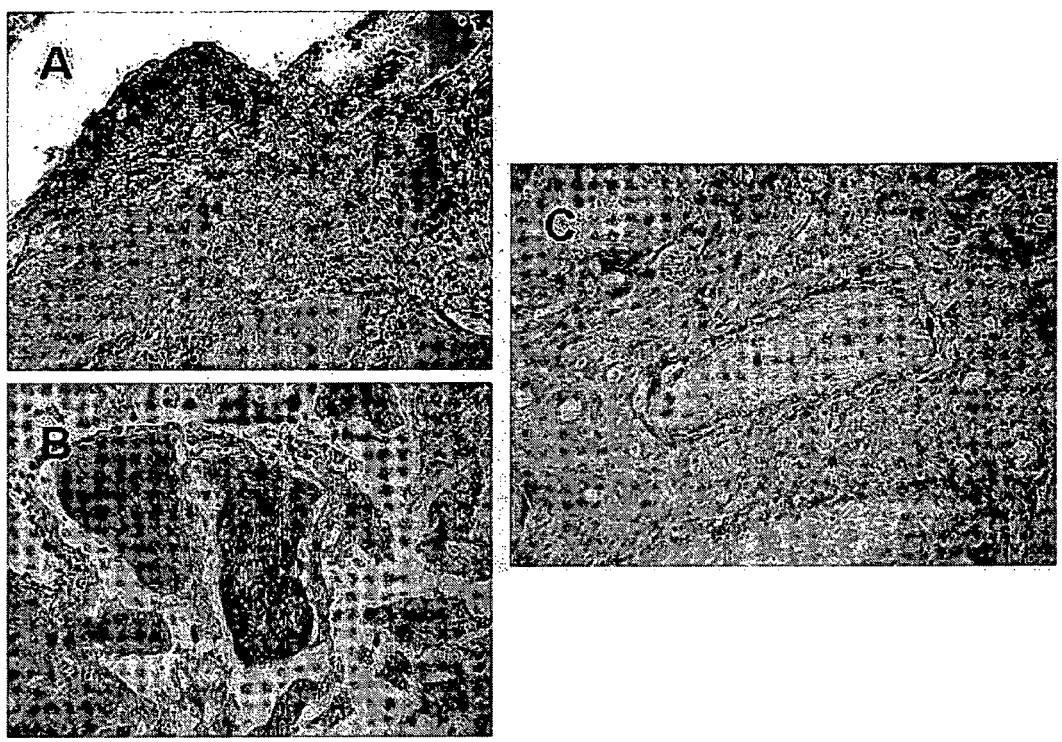
FIG. 9 shows osteogenic cells differentiated from human adipose tissue-derived multipotent stem cells according to the present invention. A: a group treated with TCP alone; B: a group treated with a mixture of TCP and marrow stem cells; and C: a group treated with a mixture of TCP and adipose-derived stem cells.

Differentiation of Adipose-Derived Multipotent Stem Cells into Osteogenic Cells $10^7$ cells/ml of the adipose tissue-derived adult stem cells obtained in Example 1 were mixed with TCP (tricalcium phosphate) and isotransplanted subcutaneously into dogs. After 14 days, the tissue was treated and analyzed using the H&E stain method. As a result, as shown in FIG. 9, a group (A) treated with TCP alone showed the permeation of inflammatory cells into a portion around TCP, and a group (B) treated with a mixture of TCP and marrow stem cells showed inflammatory responses remaining intact around TCP. However, in a group (C) treated with a mixture of TCP and adipose-derived stem cells, most of TCP was absorbed, and typical initial osteogenesis was observed, and osteoblast-like cells, multinuclear osteoclast-like cells and bone matrixes were also observed. These results indicate that the human adipose tissue-derived multipotent stem cells were differentiated into osteogenic cells.

Example 10

Figure 10:
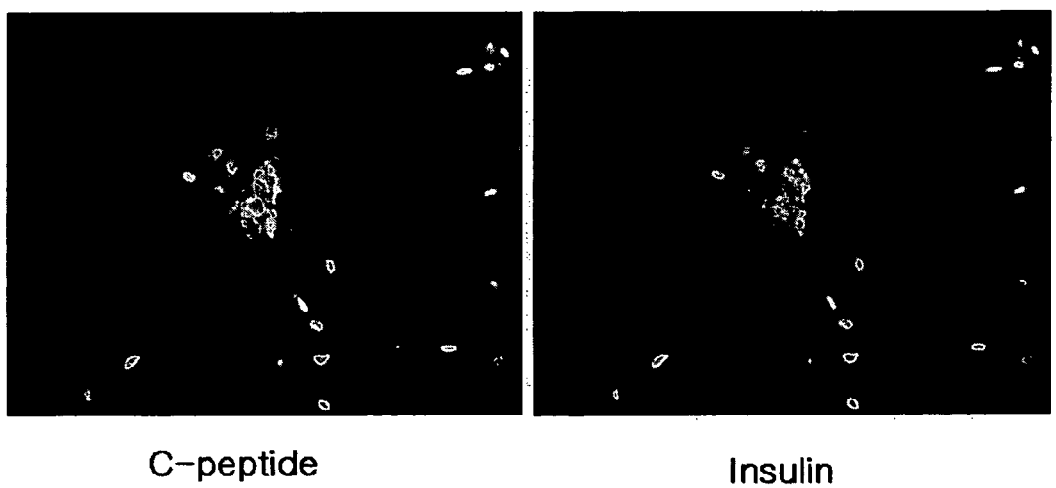
FIG. 10 shows immunostaining results for insulin-releasing pancreatic beta-cells differentiated from human adipose tissue-derived multipotent stem cells according to the present invention.

Differentiation of Adipose-Derived Multipotent Stem Cells into Insulin-Releasing Pancreatic Beta-Cells The adipose tissue-derived multipotent stem cells obtained in Example 1 were incubated in low-glucose DMEM medium containing 10 mmol/L nicotinamide, 1 mmol/L β-mercaptoethanol and 10% FBS for 24 hours, and then incubated in high-glucose DMEM medium containing 10 mmol/L nicotinamide, 1 mmol/L β-mercaptoethanol and 5% FBS for 5 days, so as to induce differentiation into insulin-releasing pancreatic beta-cells. After inducing the differentiation, the cells were analyzed by immunostaining, and the results are shown in FIG. 10. As shown in FIG. 10, C-peptide and insulin were present in the cells. As known in the art, proinsulin, which is divided into insulin and C-peptide, is produced in insulin-releasing pancreatic beta-cells. Thus, the above results indicate that the adipose tissue-derived multipotent stem cells according to the present invention were differentiated into insulin-releasing pancreatic beta-cells.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described in detail above, although the multipotent stem cells according to the present invention are adult stem cells, they can differentiate into more various kinds of cells than those differentiated from the prior adipose-derived adult stem cells. Particularly, the inventive adult multipotent stem cells have the ability to differentiate into nerve cells, astrocytes, fat cells, chondrogenic cells, osteogenic cells, or insulin-releasing pancreatic beta-cells, and are effective in treating osteoporosis, osteoarthritis, nerve disease, diabetes, etc., and also useful for the formation of breast tissue. Also, the inventive adult stem cells form spheres in a serum-free medium, so that they can be isolated with high purity, maintained in an undifferentiated state for a long period of time and have a high proliferation rate. Thus, the inventive adult stem cells are useful as cellular therapeutic agents.

What is claimed is:

1. A method for producing a homogenous cell population of mesenchymal stem cells, comprising:
   culturing human adipose tissue-derived pellets in a medium containing N-acetyl-L-cysteine (NAC);
   removing unattached cells from the culture;
   culturing the remaining attached cells in a medium containing NAC to produce a homogenous population of human adipose tissue-derived mesenchymal stem cells wherein the cells are characterized by:
   (a) showing positive immunological responses to all of CD73, CD90, CD29, CD44 and CD105, and negative immunological responses to all of CD33, CD34, CD45, CD4, CD31, CD62p, CD14 and HLA-DR;
   (b) growing attached to a plastic material, showing spindle-shaped morphological features, and forming spheres in a medium containing CORM-2 so as to be able to be maintained in an undifferentiated state; and
   (c) having the ability to differentiate into cells selected from the group consisting of mesoderm-derived cells, nerve cells, and pancreatic cells.

2. The method according to claim 1, wherein the NAC-containing medium additionally contains ascorbic acid, calcium, rEGF, BPE, insulin and hydrocortisone.

3. A method for maintaining a homogenous cell population including mesenchymal stem cells in an undifferentiated state, the method comprising culturing mesenchymal stem cells prepared by the method according to claim 1, in a medium containing CORM-2 so as to form spheres.

4. The method according to claim 3, wherein the CORM-2-containing medium is a serum-free medium which additionally contains antibiotic antimycotic solution, hydrocortisone, insulin, rEGF, FGF, B27 and β-mercaptoethanol.

* * * * *